(12) United States Patent
Dekeyser et al.

(10) Patent No.: US 6,297,275 B1
(45) Date of Patent: Oct. 2, 2001

(54) METHOD FOR CONTROLLING FUNGI USING PHENYLHYDRAZINE DERIVATIVES

(75) Inventors: Mark Achiel Dekeyser, Waterloo (CA); Kenneth Wesley Seebold, Jr., Naugatuck, CT (US); Gaik-Lean Chee, Guelph (CA)

(73) Assignees: Uniroyal Chemical Company, Inc.; Crompton Co./Cie

( * ) Notice: Subject to any disclaimer, the term of this patent is extended or adjusted under 35 U.S.C. 154(b) by 0 days.

(21) Appl. No.: 09/391,292

(22) Filed: Sep. 7, 1999

(51) Int. Cl.$^7$ .......................... A01N 47/10; A01N 37/18; A01N 47/40
(52) U.S. Cl. .......................... 514/486; 514/478; 514/482; 514/485; 514/488; 514/614
(58) Field of Search .................................... 514/478, 482, 514/485, 486, 488, 614

(56) References Cited

U.S. PATENT DOCUMENTS 5,367,093    11/1994    Dekeyser et al. ................. 560/27

OTHER PUBLICATIONS

"Fungicidal arylhydrazine derivatives", Frohberger et al, Chemical Abstracts 80:70557n (1974).
"Hydrazine Carboxylates", Haga et al, Chemical Abstracts 104:33894p (1986).
"Preparation of phenylcarbazates as agrochemical fungicides", Takematsu et al, Chemical Abstracts 114:138036v (1991).
"Benzyl carbazates and agrochemical microbicides containing them", Takematsu et al, Chemical Abstracts 115:226148j (1991).

Primary Examiner—Allen J. Robinson
(74) Attorney, Agent, or Firm—Daniel Reitenbach

(57) ABSTRACT

A method for controlling fungi using a phenylhydrazine derivative compound of the formula:

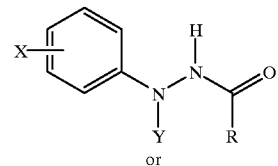

(I)

or

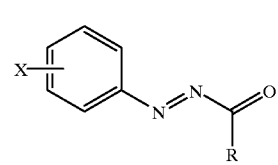

(II)

wherein:
- X is phenyl, phenylalkoxy, phenoxy, or benzyl, alone or in combination with one or more halogen, alkyl, or alkylthio;
- Y is hydrogen, alkanoyl, haloalkanoyl, or alkoxy carbonyl; and
- R is hydrogen, alkyl, haloalkyl, alkoxy, haloalkoxy, or phenylalkoxy.

8 Claims, No Drawings

METHOD FOR CONTROLLING FUNGI USING PHENYLHYDRAZINE DERIVATIVES

FIELD OF THE INVENTION

This invention relates to a method for controlling fungi using certain phenylhydrazine derivatives. More particularly, this invention relates to a method for controlling fungi by contacting the fungi with a fungicidally effective amount of a phenylhydrazine derivative compound, or by applying the phenylhydrazine derivative compound to plant foliage or plant seed susceptible to attack by said fungi, or to a growth medium for the plant to be protected.

BACKGROUND OF THE INVENTION

U.S. Pat. No. 5,367,093 describes phenylhydrazine derivative compounds useful as insecticides, acaricides and nematocides. Japanese patent JP02300157 1990 (CA 115:226148) describes benzyl carbazates useful as agrochemical microbiocides. Japanese patent JP02295962 1990 (CA 114:138036) describes the preparation of phenyl carbazates useful as agrochemical fungicides. Japanese patent JP60161959 1985 (CA 104:33894) describes hydrazine carboxylates useful as fungicides. German patent DE2223936 1973 (CA 80:70557) describes fungicidal arylhydrazine derivatives.

It is an object of this invention to provide a novel method for controlling fungi using phenylhyrazine derivative compounds and compositions.

SUMMARY OF THE INVENTION

This invention relates to a method for controlling fungi, particularly phytopathogenic fungi, comprising contacting the fungi with a fungicidally effective amount of a phenylhydrazine derivative compound of the formula:

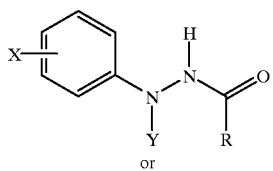

(I)

or

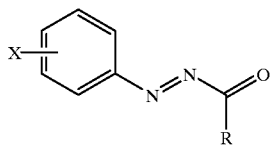

(II)

wherein:

X is a) phenyl; phenyl($C_1$–$C_4$ alkoxy); phenoxy; or benzyl; or b) one substituent from group a) and one or more substituents selected from halogen; $C_1$–$C_4$ alkyl; and $C_1$–$C_4$ alkylthio;

Y is H, $C_1$–$C_4$ alkanoyl, $C_1$–$C_4$ haloalkanoyl, or ($C_1$–$C_4$ alkoxy)carbonyl; and R is H, $C_1$–$C_6$ alkyl, $C_1$–$C_6$ haloalkyl, $C_1$–$C_6$ alkoxy, $C_1$–$C_6$ haloalkoxy, or phenyl ($C_1$–$C_4$ alkoxy).

This invention also relates to a method for controlling fungi on a plant or plant seed which comprises applying to the plant or the plant seed, or to a growth medium or water in which the plant or plant seed is growing or is to be grown in, a fungicidally effective amount of a phenylhydrazine derivative compound of the formula:

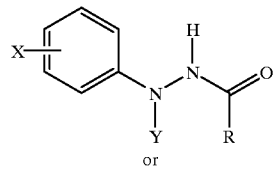

(I)

or

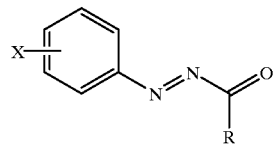

(II)

wherein:

X is a) phenyl; phenyl($C_1$–$C_4$ alkoxy); phenoxy; or benzyl; or b) one substituent from group a) and one or more substituents selected from halogen; $C_1$–$C_4$ alkyl; and $C_1$–$C_4$ alkylthio;

Y is H, $C_1$–$C_4$ alkanoyl, $C_1$–$C_4$ haloalkanoyl, or ($C_1$–$C_4$ alkoxy)carbonyl; and R is H, $C_1$–$C_6$ alkyl, $C_1$–$C_6$ haloalkyl, $C_1$–$C_6$ alkoxy, $C_1$–$C_6$ haloalkoxy, or phenyl($C_1$–$C_4$ alkoxy).

DETAILED DESCRIPTION OF THE INVENTION

For the purposes of this invention, the term "controlling fungi" means inhibiting both future infestation and continued growth of existing infestations.

In the compounds useful in the method of this invention, X is preferably, a) phenyl, phenyl($C_1$–$C_2$ alkoxy), or phenoxy; or b) one substituent from group a) and one or more substituents selected from halogen; $C_1$–$C_2$ alkyl; and $C_1$–$C_2$ alkylthio;

Y is preferably H, $C_1$–$C_2$ alkanoyl, $C_1$–$C_2$ haloalkanoyl, or ($C_1$–$C_2$ alkoxy)carbonyl; and R is preferably H, $C_1$–$C_4$ alkyl, $C_1$–$C_4$ haloalkyl, $C_1$–$C_4$ alkoxy, $C_1$–$C_4$ haloalkoxy, or phenyl($C_1$–$C_2$ alkoxy).

X is more preferably phenylmethoxy, phenoxy, or phenyl and halogen or $C_1$–$C_4$ alkylthio, most preferably, phenoxy; Y is more preferably hydrogen or $C_1$–$C_2$ haloalkanoyl, most preferably, hydrogen; and R is more preferably $C_1$–$C_4$ alkoxy or $C_1$–$C_4$ haloalkoxy, most preferably, $C_1$–$C_4$ alkoxy.

The compounds useful in the method of this invention having the structure of formula I can be prepared by reacting a substituted phenylhydrazine of the formula:

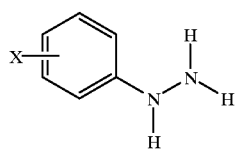

with an acylating reagent of the formula:

wherein Z is halo or

and an equivalent of an HCl acceptor such as pyridine in a solvent such as toluene. The product of this reaction can be further acylated, or converted by oxidation with an oxidizing agent such as Pd/air to form compounds of the structure of formula II.

Compositions useful in the method of this invention comprise (a) a fungicidally effective of a compound having a structure of formula (I) or (II) above, and (b) a suitable carrier. Such suitable carriers may be solid or liquid in nature.

Suitable liquid carriers may be comprised of water, alcohols, ketones, phenols, toluene and xylenes. In such formulations, additives conventionally employed in the art may be utilized such as, for example, one or more surface active agents and/or inert diluents, to facilitate handling an application of the resulting pesticide composition.

The compositions useful in the method of this invention can alternatively comprise solid carriers taking the form of dusts, granules, wettable powders, pastes, aerosols, emulsions, emulsifiable concentrates, and water-soluble solids.

For example, the compounds useful in the method of this invention can be applied as dusts when admixed with or absorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, soil incorporation or seed treatment, are suitably prepared using a granular or pellitized form of carrier such as granular clays, vermiculite, charcoal or corn cobs.

Alternatively, the compounds useful in the method of this invention can be applied in liquids or sprays when utilized in a liquid carrier, such as in a solution comprising a compatible solvent such as acetone, benzene, toluene or kerosene, or as dispersed in a suitable non-solvent medium, for example, water.

Another method of application to the loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For treatment of plants (such term including plant parts), the compounds useful in the method of this invention preferably are applied in aqueous emulsions containing a surface-active dispersing agent which may be non-ionic, cationic or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which are pesticidally active, such as insecticides, acaricides, fungicides or bactericides.

It will be understood that the amount of the compound in a given formulation useful in the method of this invention will depend upon the specific fungus to be combatted, as well as upon the specific chemical composition and formulation of the compound being employed, the method of applying the compound/formulation and the locus of treatment so that the fungicidally effective amount of the compound may vary widely. Generally, however, concentrations of the compound as the active ingredient in fungicidally effective formulations in the method of this invention can range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, tobacco, rice and the like.

To control fungi, sprays of the compounds can be applied to the fungi directly and/or to plants or plant seeds upon which they feed or nest. The fungicidally active formulations useful in the method of this can also be applied to the soil, water, or other growth medium in which the pests are present.

The specific methods of application, as well as the selection and concentration of the compounds useful in the method of this invention, will, of course, vary depending upon such circumstances as geographic area, climate, topography, plant tolerance, etc. For specific circumstances, one skilled in the art may readily determine the proper compound, concentration and method of application by routine experimentation.

Examples of phytopathogenic fungi which can be controlled by the method of this invention include, e.g., the following:

*Erysiphe graminis* f.sp. *hordei*
*Erysiphe cichoracearum*
*Erysiphe polygoni*
*Pyricularia grisea*
*Helminthosporium sativum*
*Uromyces appendiculatus*
*Botrytis cinerea*
*Colletotrichum gossypii*
*Cercosporidium personatum*
*Fusarium nivale*
*Phytopthora infestans*
*Pythium ultimum*
*Rhizoctonia solani*
*Sclerotinia minor*
*Septoria nodurum*

EXAMPLES

The following examples are provided to further illustrate the invention.

Example 1

Preparation of 2,2,2-trichloroethyl 2-(4-phenylmethoxy)-phenylhydrazine carboxylate (Compound 1)

To 2.72 g of 4-(phenylmethoxy)phenylhydrazine, 100 ml of ethyl acetate and 2.5 ml of pyridine were added and the resulting solution was stirred at room temperature for 60 minutes. Then, 2.3 ml of 2,2,2-trichloroethyl chloroformate was added dropwise to the solution and then stirred for 1 hour at room temperature. The solution was then washed twice, each time with 100 ml of water. After each wash, the aqueous fraction was removed from the organic (ethyl acetate) fraction. The resulting ethyl acetate fraction was then dried over anhydrous sodium sulfate, evaporated under reduced pressure, and then purified by column chromatography on silica gel, to produce 0.5 g of 2,2,2-trichloroethyl 2-(4-phenyl-methoxy)phenylhydrazine carboxylate as an oil.

Example 2

Preparation of 2,2,2-trichloroethyl 2-(4-phenylmethoxy)-2-(trifluoroacetyl)phenylhydrazine carboxylate (Compound 2)

To 0.5 g of the product of Example 1 was added 25 ml of dichloromethane and 0.5 ml of trifluoroacetic anhydride. The resultant reaction mixture was then stirred at room temperature for 4 hours, concentrated under reduced pressure, and the concentrate isolated, to produce 0.6 g of 2,2,2-trichloroethyl 2-(4-phenylmethoxy)-2-(trifluoroacetyl)phenylhydrazine carboxylate as a solid.

Example 3

Preparation of 1-methyloropyl 2-(3-phenoxyphenyl)-hydrazine carboxylate (Compound 3)

To 3.0 g of 3-phenoxyphenyl hydrazine, 100 ml of ethyl acetate and 2.5 ml of pyridine were added and the resultant solution was then stirred at room temperature for 30 minutes. Then, 2.5 ml of sec-butyl chloro-formate was added dropwise to the solution and stirred for 1 hour at room temperature. The solution was then washed twice, each time with 100 ml of water. After each wash, the aqueous fraction was removed from the organic (ethyl acetate) fraction. The resulting ethyl acetate fraction was then dried over anhydrous sodium sulfate, evaporated under reduced pressure, and then purified by column chromatography on silica gel, to produce 1.5 g of 1-methylpropyl 2-(3-phenoxyphenyl) hydrazine carboxylate as an oil.

The remaining compounds listed in Table 1A (i.e., Compounds 4–6) were prepared using the same procedures as shown in the foregoing examples 1–3 using the correspondingly different substituted phenylhydrazine. Each of the compounds is characterized by their NMR characteristics.

TABLE 1A

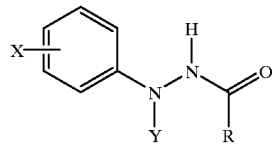

| Cmpd | X | Y | R | NMR DATA (CDCl$_3$) |
|---|---|---|---|---|
| 1 | 4-OCH$_2$C$_6$H$_5$ | H | OCH$_2$CCl$_3$ | s(2)4.7; s(2)4.9; s(1)5.7; m(10)6.8–7.4 |
| 2 | 4-OCH$_2$C$_6$H$_5$ | CF$_3$CO | OCH$_2$CCl$_3$ | s(2)4.8; s(2)4.9; m(9)6.9–7.5 |
| 3 | 3-OC$_6$H$_5$ | H | OCH(CH$_3$)C$_2$H$_5$ | t(3)0.8; d(3)1.2; m(2)1.5; m(1)4.8; s(1)6.5; m(10)6.9–7.4 |
| 4 | 2-Br, 5-C$_6$H$_5$ | H | OCH$_3$ | s(3)3.8; s(1)6.5; m(10)6.9–7.5 |
| 5 | 2-SCH$_3$, 5-C$_6$H$_5$ | H | OCH$_3$ | s(3)2.4; s(1)6.5; m10)7.0–7.5 |
| 6 | 4-OC$_6$H$_5$ | H | OCH$_2$C$_6$H$_5$ | s(2)5.1; s(1)6.5; m(15)6.8–7.4 |

Example 4

Preparation of 1-methylpropyl (3-phenoxyohenyl) diazene carboxylate (Compound 7)

To 1.5 g of the product of Example 3 was added 100 ml of toluene and 0.4 g of 10% palladium on charcoal. The resultant mixture was stirred overnight at room temperature, filtered, and the toluene evaporated under reduced pressure, to produce 1.3 g of 1-methyl-propyl(3-phenoxyphenyl) diazene carboxylate as a red oil.

TABLE 1B

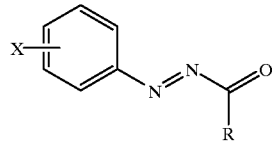

| Cmpd | X | R | NMR DATA (CDCl$_3$) |
|---|---|---|---|
| 7 | 3-OC$_6$H$_5$ | OCH(CH$_3$)C$_2$H$_5$ | t(3)1.0; m(2)1.5; m(1)5.0; m(9)7.0–7.5 |

Preparation of Fungicidal Compositions

The compounds listed below in Table 3 were each dissolved in acetone or another suitable solvent (0.3 grams of each compound in 10 ml of acetone or other suitable solvent). One to two drops of Tween 20®, a polyoxyethylene sorbitan ester used as an emulsifying agent, were added to water, followed by the acetone solution containing one of the compounds listed in Table 3. The amount of water added to the final solution varied according to the desired concentration, reported in parts per million (ppm).

Control of Powdery Mildew by Foliar Application

The barley cultivar 'Rodeo' was seeded into 4-inch-diameter pots containing a suitable medium for plant growth and allowed to grow for six days. Each treatment, or chemical, listed in Table 3 was replicated twice, and each pot contained eight plants. For each test, two pots of barley were left untreated to serve as controls.

Each of the compounds tested was formulated as described previously at a concentration of 1000 mg of compound per liter of water (1000 ppm), or 300 mg of compound per liter of water (300 ppm) in the case of Compound 2 and Compound 5. The resultant emulsion was applied to the foliage of the barley using an atomizer pressurized to 25–30 pounds per square inch. The treated plants, along with the untreated controls, were placed in a greenhouse and held at 21–25° C. One day following treatment, all plants were inoculated with conidia of *Erysiphe graminis* f.sp. *hordei* by brushing the leaves of mildew-infected barley plants over the leaves of the treated plants. One week after treatment, plants were rated for symptoms of powdery mildew using a 0–6 scale where 0=no disease and 6=severe symptoms of mildew. Percent control was computed by comparing disease ratings of treated plants to those from untreated plants. The results of these tests are provided in Table 4A under the heading "Barley PM".

The compounds in Table 3 were tested for the control of powdery mildew of bean, caused by *Erysiphe polygoni* by preparing pots containing pinto bean (*Phaseolus vulgaris*) in the same manner as described for barley. Methods for application of the chemical, inoculation with the pathogen, and rating of disease were identical to those described in the previous paragraph. The results of these tests are located in Table 4A under the heading "Bean PM".

Control of Powdery Mildew by Systemic Root Uptake

Compounds listed in Table 3 were prepared as described previously and tested for efficacy against powdery mildew of barley, caused by *Erysiphe graminis* f.sp. *hordei,* and powdery mildew of cucumber, caused by *Erysiphe cichoracearum*. Each compound was evaluated for prevention or control of powdery mildew when applied as a soil drench, resulting in uptake of the compounds in question by the roots of barley or cucumber and then systemic distribution to the foliage.

Pots of barley (cv. "Robust") or cucumber (cv. "Marketmore 70") were grown in the same manner as barley plants used for foliar applications. Pots containing barley had eight plants, while pots containing cucumber held two plants. Approximately one week after planting, 45 ml of an emulsion composition, formed as described previously, was added to pots containing either barley or cucumber. Specifically, each 45ml of each compound was drenched into the soil of two pots containing barley and two pots containing cucumber at a rate of 250 g of compound per liter of water (250 ppm). Two compounds, Compound 2 and Compound 5, were tested at a concentration of 300 g of compound per liter of water (300 ppm). Two pots each of barley and cucumber were left untreated to serve as controls for the experiment. Inoculation of the plants was carried out as described previously, and plants were rated for symptoms of powdery mildew one week following treatment using a 0–6 scale where 0=no disease and 6=severe symptoms of powdery mildew. Percent control was calculated by comparing ratings of treated plants to those from untreated plants. Results of these tests are found in Table 4B under the headings "Barley PM" and "Cucumber PM".

Control of Barley Blast by Foliar Treatment

Five barley plants (cv. "Rodeo") were grown in 4-inch-diameter pots, with two replicates for each treatment. An untreated check was also included and was replicated twice. Non-control pots were sprayed with emulsion compositions prepared as described previously, with each composition being tested at a concentration of 1000 ppm. Compound 2 and Compound 5 were tested at a concentration of 300 ppm. The average plant age was 10 days. Twenty-four hours after application of the compositions, treated and untreated pots were inoculated with the pathogen, *Pyricularia grisea,* at a concentration of 40,000 to 50,000 conidia $ml^{-1}$ as a foliar spray. Tween 20® was added (0.05% v/v) to aid in wetting of the foliage, and plants were sprayed to runoff with the conidial suspension.

All inoculated pots were placed in an environmental chamber set to maintain 26° C. and >95% relative humidity. Barley plants were incubated for 24 hours in the chamber, after which they were transferred to a greenhouse and observed for the development of symptoms of blast (6–7 days post-inoculation). Disease was evaluated using a 0–6 rating scale where 0=no blast lesions present and 6=severe symptoms. Percent control of blast was calculated by comparing ratings of treated plants to those from untreated plants. The results of these tests are located in Table 4A under the heading "Barley Blast".

Control of Barley Spot Blotch by Foliar Treatment

Two pots, each containing 10 barley plants (cv. Robust), were planted. Plants were treated with the previously described compositions that had been formulated in the same manner as for earlier examples. Treated and untreated (control) pots were then inoculated with an aqueous inoculum suspension consisting of 20,000 conidia $ml^{-1}$ of *Helminthosporium sativum* and 2 drops of Tween 20® per 100 ml of solution were added to improve wetting. The inoculation and incubation procedure was identical to that used in barley blast tests.

Inoculated plants were then placed in a greenhouse and observed for development of symptoms, normally 6–7 days post-inoculation. Disease was evaluated using a 0–6 rating scale where 0=no blotch lesions present and 6=severe symptoms. Percent control was determined by comparing ratings from treated plants to ratings from untreated control plants. Results for these are located in Table 4A "Barley Blotch".

Eradication of Bean Rust by Foliar Application

Two pinto bean plants (*Phaseolus vulgaris*) were planted in 4-inch-diameter pots and replicated twice. Ten days after planting, when primary leaves had emerged, plants to be treated or left untreated as controls were inoculated with an aqueous suspension of uredospores of the bean rust pathogen, *Uromyces appendiculatus*. The inoculum was adjusted to a concentration of 20,000 uredospores $ml^{-1}$, and 2 drops of Tween 20® per 100 ml of solution were added to improve wetting. Inoculated plants were then placed in an environmental chamber set to maintain 26° C. and >95% relative humidity. Twenty-four hours after inoculation, plants were removed and treated with the previously described fungicidal compositions at identical rates. Two pots were left untreated to serve as controls. Immediately following treatment, plants were placed in a greenhouse and observed for symptom development (5–7 days after inoculation). Disease was assessed on a 0–6 rating scale, where 0=no symptoms and 6=severe symptoms of bean rust. Percent control was calculated by comparing disease ratings from treated plants to ratings from untreated plants. The results of these experiments are detailed in Table 4A under the heading "Bean Rust".

TABLE 4A

Percent control of phytopathogenic fungi in vivo.
Foliar Application

| Cmpd | Barley PM | Barley Blast | Bean PM | Barley Blotch | Bean Rust |
|---|---|---|---|---|---|
| | 1000 ppm | 1000 ppm | 1000 ppm | 1000 ppm | 1000 ppm |
| 1 | 0 | 0 | 0 | 0 | 0 |
| 3 | 90 | 70 | 90 | 100 | 0 |
| 4 | 0 | 65 | 100 | 100 | 85 |
| 6 | 0 | 0 | 0 | 0 | 0 |
| 7 | 0 | 35 | 100 | 70 | 0 |
| | 300 ppm | 300 ppm | 300 ppm | 300 ppm | 300 ppm |
| 2 | 0 | 0 | 0 | 0 | 0 |
| 5 | 0 | 0 | 0 | 0 | 0 |

TABLE 4B

Percent control of phytopathogenic fungi in vivo.
Drench Application

| Cmpd | Barley PM | Cucumber PM |
|---|---|---|
| | 250 ppm | 250 ppm |
| 1 | 0 | 0 |
| 3 | 0 | 0 |
| 4 | 0 | 0 |
| 6 | 0 | 0 |
| 7 | 20 | 0 |
| | 300 ppm | 300 ppm |
| 2 | 0 | 0 |
| 5 | 0 | 0 |

Control of Nine Species of Fungi in vitro

Each of the compounds listed in Table 3, with the exception of Compound 5, was solubilized in acetone to arrive at a final concentration of 500 ppm. Filter paper disks with a diameter of 11 mm were immersed in each of the test solutions and then allowed to air-dry so that the solvent evaporated from the disk. Two disks per treatment were prepared, and an equal number of disks were left untreated to serve as controls.

Treated and untreated disks were then placed on 110×15 mm petri plates containing solidified potato-dextrose agar (PDA). A sufficient number of treated and untreated disks were prepared to allow testing of all fungicidal compositions for the control of Botrytis cinerea (B. cinerea), Colletotrichum gossyppii (C. gossypii), Cercosporidium personatum (C. personatum), Fusarium nivale (F. nivale), Phytopthora infestans (P. infestans), Pythium ultimum (P. ultimum), Rhizoctonia solani (R. solani), Sclerotinia minor (S. minor), and Septoria nodurum (S. nodurum). Treated and untreated disks were inoculated by placing a 6 mm plug, cut from an actively growing area of a culture of each of the fungi listed, in the center of the disk. The plug was oriented on the disk so as to allow the mycelial mat of the plug to contact the treated or untreated disk. In the case of C. personatum, two drops of a conidial/mycelial suspension, adjusted to a concentration of 20,000 propagules per $ml^{-1}$, were placed on the surface of untreated and treated disks.

The plates containing the inoculated disks were then placed in a gravity-type incubator set at 25° C. and incubated for 5–7 days. Growth inhibition was evaluated by measuring the radius of the fungal colonies emanating from the original plug of inoculum on treated disks and comparing these measurements with those taken from untreated disks. The results of in vitro testing are located in Tables 5A and 5B.

In the case of Compound 5, a different method was used to assay fungicidal activity against the previously listed fungal species. A stock solution of each of the fungicidal compositions previously described was prepared by dissolving 0.01 g of the compound into 0.75 ml of acetone to achieve a final concentration of 15,000 ppm. A 1 $\mu l$ drop of each of the test compounds was then added to individual wells in a 96-well microtiter plate containing 50 $\mu l$ of potato-dextrose broth. Four wells in each plate were left untreated to serve as controls.

A suspension containing 10,000 cell fragments or conidia $ml^{-1}$ (depending upon the fungus) was prepared by scraping petri plates containing active cultures of each of the test fungi with a rubber policeman, and homogenizing the resultant suspension with a glass tissue grinder. The final concentration was measured using a hemacytometer, and 50 $\mu l$ of the fungal suspension was added to each of the wells in the previously treated microtiter plate. Separate plates were used for each fungus, and the final concentration of test chemical was 150 ppm. Prior to incubation, each plate was placed on an eight-channel photometric microplate reader, set to measure absorbence at 492 nm, and an initial reading was taken to establish a baseline for each cell in the microplate.

Microtiter plates were then incubated for 48 hours in an incubation chamber set to maintain 26° C. to allow for optimal growth of the test fungi. Following incubation, the microtiter plates containing the test fungi were removed and evaluated with the photometric microplate reader described earlier. In principle, as fungal growth increases, the optical density of the solution in the individual wells of the microplate increases and can be measured photometrically. Therefore, readings taken following incubation of the microplates containing test chemicals and fungi were subtracted from the initial readings to measure the amount of growth over the 48-hour period. Percent inhibition of each fungus by the test chemicals was calculated by comparing absorbence values from treated wells to those that were untreated. The results of this testing of Compound 5 can be found in Tables 5A and 5B.

TABLE 5A

Percent control of phytopathogenic fungi in vitro.

| Cmpd | B. cinerea | C. gossypii | C. personatum | F. nivale | P. infestans |
|---|---|---|---|---|---|
| | 500 ppm | 500 ppm | 500 ppm | 500 ppm | 500 ppm |
| 1 | 10 | 80 | 0 | 0 | 85 |
| 2 | 91 | 100 | 100 | 10 | 0 |
| 3 | 85 | 100 | 0 | 84 | 100 |
| 4 | 100 | 100 | 100 | 100 | 80 |

TABLE 5A-continued

Percent control of phytopathogenic fungi in vitro.

| Cmpd | B. cinerea | C. gossypii | C. personatum | F. nivale | P. infestans |
|---|---|---|---|---|---|
| 6 | 85 | 100 | 0 | 100 | 60 |
| 7 | 100 | 100 | 100 | 100 | 100 |
|  | 150 ppm | 150 ppm | 150 ppm | 150 ppm | 150 ppm |
| 5 | 90 | 10 | 0 | 70 | 45 |

TABLE 5B

Percent control of phytopathogenic fungi in vitro.

| Cmpd | P. ultimum | R. solani | S. minor | S. nodurum |
|---|---|---|---|---|
|  | 500 ppm | 500 ppm | 500 ppm | 500 ppm |
| 1 | 100 | 5 | 0 | 25 |
| 2 | 47 | 0 | 5 | — |
| 3 | 100 | 78 | 100 | 90 |
| 4 | 100 | 70 | 100 | 75 |
| 6 | 45 | 0 | 100 | 0 |
| 7 | 70 | 75 | 100 | 100 |
|  | 150 ppm | 150 ppm | 150 ppm | 150 ppm |
| 5 | 0 | 85 | 45 | — |

What is claimed is:

1. A method for controlling fungi comprising contacting the fungi with a fungicidally effective amount of a phenylhydrazine derivative compound of the formula:

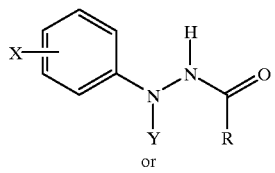

(I)

or

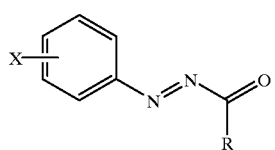

(II)

wherein:
X is a) phenyl; phenyl($C_1$–$C_4$ alkoxy); phenoxy; or benzyl; or b) one substituent from group a) and one or more substituents selected from halogen; $C_1$–$C_4$ alkyl; and $C_1$–$C_4$ alkylthio;
Y is H, $C_1$–$C_4$ alkanoyl, $C_1$–$C_4$ haloalkanoyl, or ($C_1$–$C_4$ alkoxy)carbonyl; and
R is H, $C_1$–$C_6$ alkyl; $C_1$–$C_6$ haloalkyl, $C_1$–$C_6$ alkoxy, $C_1$–$C_6$ haloalkoxy, or phenyl ($C_1$–$C_4$ alkoxy).

2. The method as recited in claim 1 wherein
X is a) phenyl; phenyl($C_1$–$C_2$)alkoxy; or phenoxy; or b) one substituent from group a) and one or more substituents selected from halogen; $C_1$–$C_2$ alkyl; and $C_1$–$C_2$ alkylthio;
Y is H, $C_1$–$C_2$ alkanoyl, $C_1$–$C_2$ haloalkanoyl, or ($C_1$–$C_2$ alkoxy)carbonyl; and
R is H, $C_1$–$C_4$ alkyl, $C_1$–$C_4$ haloalkyl, $C_1$–$C_4$ alkoxy, $C_1$–$C_4$ haloalkoxy, or phenyl ($C_1$–$C_4$ alkoxy).

3. The method as recited in claim 2 wherein X is phenylmethoxy, phenoxy, or phenyl and halogen or $C_1$–$C_2$ alkylthio; Y is hydrogen or $C_1$–$C_2$ haloalkanoyl; and R is $C_1$–$C_4$ alkoxy or $C_1$–$C_4$ haloalkoxy.

4. The method as recited in claim 3 wherein X is phenoxy; Y is hydrogen; and R is $C_1$–$C_4$ alkoxy.

5. A method for controlling fungi on a plant or plant seed wherein the plant or plant seed is infected by fungi, which method comprises applying to the plant or the plant seed, or to a growth medium or water in which the plant or plant seed is growing or is to be grown in, a fungicidally effective amount of a phenylhydrazine derivative compound of the formula:

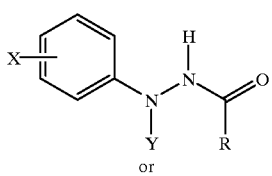

(I)

or

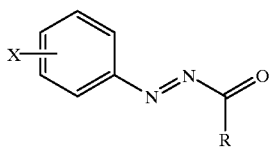

(II)

wherein:
X is a) phenyl; phenyl($C_1$–$C_4$ alkoxy); phenoxy; or benzyl; or b) one substituent from group a) and one or more substituents selected from halogen; $C_1$–$C_4$ alkyl; and $C_1$–$C_4$ alkylthio;
Y is H, $C_1$–$C_4$ alkanoyl, $C_1$–$C_4$ haloalkanoyl, or ($C_1$–$C_4$ alkoxy)carbonyl; and
R is H, $C_1$–$C_6$ alkyl, $C_1$–$C_6$ haloalkyl, $C_1$–$C_6$ alkoxy, $C_1$–$C_6$ haloalkoxy, or phenyl($C_1$–$C_4$ alkoxy).

6. The method as recited in claim 5 wherein
X is a) phenyl; phenyl($C_1$–$C_2$)alkoxy; or phenoxy; or b) one substituent from group a) and one or more substituents selected from halogen; $C_1$–$C_2$ alkyl; and $C_1$–$C_2$ alkylthio;
Y is H, $C_1$–$C_2$ alkanoyl, $C_1$–$C_2$ haloalkanoyl, or ($C_1$–$C_2$ alkoxy)carbonyl; and
R is H, $C_1$–$C_4$ alkyl, $C_1$–$C_4$ haloalkyl, $C_1$–$C_4$ alkoxy, $C_1$–$C_4$ haloalkoxy, or phenyl ($C_1$–$C_4$ alkoxy).

7. The method as recited in claim 6 wherein X is phenylmethoxy, phenoxy, or phenyl and halogen or $C_1$–$C_2$ alkylthio; Y is hydrogen or $C_1$–$C_2$ haloalkanoyl; and R is $C_1$–$C_4$ alkoxy or $C_1$–$C_4$ haloalkoxy.

8. The method as recited in claim 7 wherein X is phenoxy; Y is hydrogen; and R is $C_1$–$C_4$ alkoxy.

* * * * *